United States Patent
Morishita et al.

(10) Patent No.: US 10,016,349 B2
(45) Date of Patent: Jul. 10, 2018

(54) OXIDATIVE HAIR DYE COMPOSITION

(71) Applicant: HOYU CO., LTD., Nagoya-shi, Aichi-ken (JP)

(72) Inventors: Nana Morishita, Aichi-ken (JP); Hiroki Takahashi, Aichi-ken (JP)

(73) Assignee: HOYU CO., LTD., Nagoya-shi (JP)

( * ) Notice: Subject to any disclaimer, the term of this patent is extended or adjusted under 35 U.S.C. 154(b) by 0 days.

(21) Appl. No.: 15/602,164

(22) Filed: May 23, 2017

(65) Prior Publication Data

US 2017/0340537 A1    Nov. 30, 2017

(30) Foreign Application Priority Data

May 25, 2016  (JP) ................. 2016-103912

(51) Int. Cl.
*A61Q 5/10*  (2006.01)
*A61K 8/34*  (2006.01)
*A61K 8/86*  (2006.01)
*A61K 8/73*  (2006.01)
*A61K 8/46*  (2006.01)
*A61K 8/41*  (2006.01)
*A61K 8/37*  (2006.01)

(52) U.S. Cl.
CPC .............. *A61K 8/347* (2013.01); *A61K 8/342* (2013.01); *A61K 8/37* (2013.01); *A61K 8/415* (2013.01); *A61K 8/463* (2013.01); *A61K 8/731* (2013.01); *A61K 8/86* (2013.01); *A61Q 5/10* (2013.01)

(58) Field of Classification Search
CPC . A61Q 5/10; A61K 8/347; A61K 8/86; A61K 8/463; A61K 8/415; A61K 8/342; A61K 8/37

See application file for complete search history.

(56) References Cited

U.S. PATENT DOCUMENTS

| | | | |
|---|---|---|---|
| 2011/0271466 A1* | 11/2011 | Ito | A61K 8/347 8/408 |
| 2015/0231056 A1* | 8/2015 | Ikeno | A61K 8/86 424/62 |

FOREIGN PATENT DOCUMENTS

JP    2008-094820 A    4/2008

* cited by examiner

*Primary Examiner* — Eisa B Elhilo
(74) *Attorney, Agent, or Firm* — Posz Law Group, PLC

(57) ABSTRACT

An oxidative hair dye composition includes an alkaline agent and an oxidant. The oxidative hair dye composition further includes (A) α-naphthol in a content of 0.005 to 0.45% by mass, (B) at least one oily component selected from a higher alcohol, an ester, and a wax that are in a liquid state at 25° C., and (C) a nonionic surfactant having a polyoxyethylene chain having a number of moles of added ethylene oxide of 20 or more.

3 Claims, No Drawings

OXIDATIVE HAIR DYE COMPOSITION

BACKGROUND OF THE INVENTION

The present invention relates to an oxidative hair dye composition containing an alkaline agent and an oxidant.

In general, as a hair cosmetic composition, there has been known a hair dye exhibiting effects by mixing a plurality of chemicals. As such a hair cosmetic composition, for example, there has been known an oxidative hair dye composed of a first agent containing an alkaline agent and an oxidative dye, and a second agent containing an oxidant such as hydrogen peroxide. The alkaline agent promotes the action of the oxidant contained in the second agent, and also improves the hair-dyeing power by swelling hair so as to improve the permeability of the dye into the hair. The oxidative dye is a compound capable of developing a color due to the oxidation polymerization caused by the oxidant contained in the second agent, and is classified into a dye intermediate and a coupler. Various types of couplers have hitherto been known; for example, Japanese Laid-Open Patent Publication No. 2008-94820 discloses an oxidative hair dye containing α-naphthol as a coupler and formulated as a cream.

SUMMARY OF THE INVENTION

However, there has been a problem that the use of α-naphthol as a coupler degrades the viscosity stability of the composition. In particular, when α-naphthol is mixed in a cream-state oxidative hair dye having a relatively low viscosity, the decrease of the viscosity occurs, and a problem such as dripping occurs when the cream-state oxidative hair dye is used.

An objective of the present invention is to provide an oxidative hair dye composition capable of improving the viscosity stability in the oxidative hair dye composition using α-naphthol.

The present invention is based on the finding that in an oxidative hair dye composition containing α-naphthol, the viscosity stability is improved by using a predetermined oily component and a predetermined surfactant in combination. The numerical values representing the contents of the components in terms of percent by mass are the numerical values in a formulation inclusive of a solubilizer such as water.

To achieve the foregoing objective and in accordance with one aspect of the present invention, an oxidative hair dye composition comprising an alkaline agent and an oxidant is provided. The oxidative hair dye composition further comprises (A) α-naphthol in a content of 0.005 to 0.45% by mass, (B) at least one oily component selected from the group consisting of a higher alcohol, an ester, and a wax that are in a liquid state at 25° C., and (C) a nonionic surfactant having a polyoxyethylene chain having a number of moles of added ethylene oxide of 20 or more.

The mass ratio of the content of the (B) component to the content of the (C) component may be 0.01 to 1.5. The viscosity of the oxidative hair dye composition at the time of use may be 3,000 to 10,000 mPa·s at 25° C. The oxidative hair dye composition may further comprise (D) a polyethylene glycol. The oxidative hair dye composition may also comprise a first agent containing the alkaline agent and being a cream formulation and a second agent containing the oxidant and being a liquid formulation. The first agent and the second agent may be mixed with each other in an airtight container at the time of use, and the first agent may further contain (E) a hydroxyalkyl cellulose or a derivative thereof.

Other aspects and advantages of the present invention will become apparent from the following detailed description illustrating by way of example the principles of the present invention.

DETAILED DESCRIPTION OF THE PREFERRED EMBODIMENTS

Hereinafter, an oxidative hair dye composition according to one embodiment of the present invention will be described. A two-part type oxidative hair dye composition is composed of a first agent and a second agent, and after the first agent and the second agent are mixed with each other, the two-part type oxidative hair dye composition is used for dyeing hair. Alternatively, the oxidative hair dye composition may also be constituted as a three-part type oxidative hair dye composition.

<Two-Part Type Oxidative Hair Dye Composition>

The two-part type oxidative hair dye composition is composed of, for example, a first agent containing an alkaline agent and an oxidative dye, and a second agent containing an oxidant and the like.

(First Agent of Two-Part Type Oxidative Hair Dye Composition)

The first agent contains, in addition to the alkaline agent and the oxidative dye, for example, (B) at least one oily component selected from a higher alcohol, an ester and a wax each being in a liquid state at 25° C., (C) a nonionic surfactant having a polyoxyethylene (hereinafter, referred to as "POE") chain having a number of moles of added ethylene oxide (hereinafter, referred to as "EO") of 20 or more, (D) a polyethylene glycol, and (E) a hydroxyalkyl cellulose or a derivative thereof. The oxidative dye is a compound capable of developing a color due to the oxidation polymerization caused by the oxidant contained in the second agent, and is classified into a dye intermediate and a coupler. The oxidative dye includes a coupler, and preferably includes a dye intermediate.

Specific examples of the dye intermediate include p-phenylenediamine, toluene-2,5-diamine (p-toluylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chloro-p-phenylenediamine, 4-amino-m-cresol, 2-amino-4-hydroxyethylaminoanisole, 2,4-diaminophenol, and a salt thereof. Specific examples of the salt include a hydrochloride and a sulfate. Only one of these specific examples of the dye intermediate may be contained alone, or two or more of these specific examples of the dye intermediate may be contained in combination.

The coupler develops a color by bonding to the dye intermediate. The oxidative hair dye composition of the present embodiment contains (A) α-naphthol as a coupler. The lower limit of the content of (A) α-naphthol in the oxidative hair dye composition, namely in the mixture of the first agent and the second agent is 0.005% by mass or more, preferably 0.01% by mass or more, and more preferably 0.05% by mass or more. When the content of (A) α-naphthol is 0.005% by mass or more, the hair-dyeing power among other things is more improved.

The upper limit of the content of (A) α-naphthol in the mixture of the first agent and the second agent is 0.45% by mass or less, preferably 0.4% by mass or less, and more preferably 0.35% by mass or less. When the content of (A) α-naphthol is 0.45% by mass or less, the stability of a formulation is improved.

The content of (A) α-naphthol in the first agent is appropriately set, and is preferably 1% by mass or less, more preferably 0.9% by mass or less, and furthermore preferably 0.8% by mass or less. When the content of (A) α-naphthol in the first agent is 1% by mass or less, the viscosity stability of the first agent is improved.

The oxidative dye preferably includes a coupler other than (A) α-naphthol from the viewpoint of providing variations of hair color tone. Specific examples of the coupler other than (A) α-naphthol include resorcin, 5-amino-o-cresol, m-aminophenol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, 1,5-dihydroxynaphthalene, and a salt thereof. Specific examples of the salt include a hydrochloride and a sulfate. Only one of these specific examples of the coupler may be contained alone, or two or more of these specific examples of the coupler may be contained in combination. The first agent may optionally contain, as the dyes other than the aforementioned oxidative dyes, the oxidative dyes listed in, for example, "The Japanese Standards of Quasi-Drug Ingredients" (published by Yakuji Nippo Ltd., June 2006).

The lower limit of the content of the whole of the oxidative dye(s) in the mixture of the first agent and the second agent is appropriately set, and is preferably 0.01% by mass or more, more preferably 0.1% by mass or more, and furthermore preferably 0.5% by mass or more. When the content of the whole of the oxidative dye(s) is 0.01% by mass or more, the hair-dyeing power among other things is more improved.

The upper limit of the content of the whole of the oxidative dye(s) in the mixture of the first agent and the second agent is appropriately set, and is preferably 10% by mass or less, more preferably 7% by mass or less, and furthermore preferably 5% by mass or less. When the content of the whole of the oxidative dye(s) is 10% by mass or less, in particular in the case where a solubilizer is used, the solubility to the solubilizer is improved.

The (B) component improves the viscosity stability of the oxidative hair dye composition containing (A) α-naphthol. The (B) component is at least one oily component selected from a higher alcohol that is in a liquid state at 25° C., an ester that is in a liquid state at 25° C., and a wax that is in a liquid state at 25° C. Specific examples of the higher alcohol that is in a liquid state at 25° C. include isostearyl alcohol, 2-octyldodecanol, decyltetradecanol, oleyl alcohol, 2-hexyldecanol, and lauryl alcohol. Specific examples of the ester that is in a liquid state at 25° C. include diisopropyl adipate, isostearyl myristate, isotridecyl myristate, isopropyl myristate, octyldocecyl myristate, cetyl octanoate, isononyl isononanoate, isodecyl isononanoate, isotridecyl isononanoate, diisopropyl sebacate, isopropyl palmitate, hexyl laurate, decyl oleate, hexyldecyl dimethyloctanoate, octyl palmitate, lauryl lactate, octyldodecyl lactate, isocetyl stearate, isocetyl isostearate, ethylene glycol dioctanoate, cetyl caprylate, glyceryl tricaprylate, neopentylglycol dicaprate, cetyl 2-ethylhexanoate, triglyderides that is in a liquid state at 25° C., and amino acid esters that is in a liquid state at 25° C. Specific examples of the triglyceride that is in a liquid state at 25° C. include glyceryl trioleate, glyceryl tristearate, glyceryl tripalmitate, glyceryl tri(caprylate/caprate/laurate), and glyceryl tri(caprylate/caprate/linoleate). Specific examples of the amino acid ester that is in a liquid state at 25° C. include di(cholesteryl/octyldodecyl) N-lauroyl-L-glutamate. Specific examples of the wax that is in a liquid state at 25° C. include jojoba oil. Among these, only one may be contained alone, or two or more thereof may be contained in combination. Among these, from the viewpoint of being more excellent in the improvement effect of the viscosity stability, a higher alcohol and an ester that is in a liquid state at 25° C. are preferable. Among the higher alcohols, from the viewpoint of being excellent in the viscosity stability, a branched higher alcohol is preferable.

The lower limit of the (B) component in the mixture of the first agent and the second agent is appropriately set, and is preferably 0.01% by mass or more, more preferably 0.05% by mass or more, and furthermore preferably 0.1% by mass or more. When the content of the (B) component is 0.01% by mass or more, the viscosity stability is more improved. The upper limit of the (B) component in the mixture of the first agent and the second agent is appropriately set, and is preferably 5% by mass or less, more preferably 4% by mass or less, and furthermore preferably 3% by mass or less. When the content of the (B) component is 5% by mass or less, the formulation stability is improved.

The lower limit of the content of the (B) component in the first agent is appropriately set, and is preferably 0.02% by mass or more, more preferably 0.1% by mass or more, and furthermore preferably 0.2% by mass or more. The upper limit of the content of the (B) component in the first agent is appropriately set, and is preferably 10% by mass or less, more preferably 8% by mass or less, and furthermore preferably 6% by mass or less. When the content of the (B) component in the first agent is specified within such a range, the stability of the formulation containing (A) α-naphthol is improved.

(C) The nonionic surfactant having a POE chain having a number of moles of added EO of 20 or more improves the viscosity stability of the oxidative hair dye composition containing (A) α-naphthol. The POE chain of the (C) component has a number of moles of added EO of 20 or more, preferably 25 or more, and more preferably 30 or more. When the number of moles of added EO is 20 or more, the viscosity stability of the oxidative hair dye composition containing (A) α-naphthol is improved. The viscosity stability of the first agent containing (A) α-naphthol is also improved. Examples of the (C) component include an ether-type nonionic surfactant, an ester-type nonionic surfactant, and an alkyl glucoside. Specific examples of the ether-type nonionic surfactant include the following each having a POE chain having a number of moles of added EO of 20 or more: POE cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, POE polyoxypropylene cetyl ether, and POE polyoxypropylene decyl tetradecyl ether.

Specific examples of the ester-type nonionic surfactant include the following each having a POE chain having a number of moles of added EO of 20 or more: POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbit tetraoleate, POE sorbit hexastearate, POE sorbit monolaurate, POE sorbit bees wax, polyethylene glycol monooleate, polyethylene glycol monostearate, and polyethylene glycol monolaurate.

Specific examples of the alkyl glucoside include the following each having a POE chain having a number of moles of added EO of 20 or more: POE methylglucoside, and POE methyl glucoside dioleate. Only one of these specific examples may be contained alone, or two or more of these specific examples may be contained in combination.

The lower limit of the content of the (C) component in the mixture of the first agent and the second agent is appropriately set, and is preferably 0.1% by mass or more, more preferably 0.5% by mass or more, and furthermore preferably 1% by mass or more. When the content of the (C) component is 0.1% by mass or more, the viscosity stability is more improved. The upper limit of the content of the (C) component in the mixture of the first agent and the second agent is appropriately set, and is preferably 20% by mass or less, more preferably 10% by mass or less, and furthermore preferably 5% by mass or less. When the content of the (C) component is 20% by mass or less, the sense of touch is improved.

The lower limit of the content of the (C) component in the first agent is appropriately set, and is preferably 0.2% by mass or more, more preferably 1% by mass or more, and furthermore preferably 2% by mass or more. The upper limit of the content of the (C) component in the first agent is appropriately set, and is preferably 40% by mass or less, more preferably 20% by mass or less, and furthermore preferably 10% by mass or less. When the content of the (C) component in the first agent is specified within such a range, a desired viscosity is imparted to the first agent containing (A) α-naphthol.

The lower limit of the mass ratio of the content of the (B) component to the content of the (C) component is preferably 0.01 or more, more preferably 0.05 or more, and furthermore preferably 0.1 or more. When such a mass ratio is set to be 0.01 or more, the viscosity stability is more improved. The upper limit of the mass ratio of the content of the (B) component to the content of the (C) component is preferably 1.5 or less, more preferably 1.2 or less, and furthermore preferably 0.9 or less. When such a mass ratio is set to be 1.5 or less, the formulation stability of the first agent containing (A) α-naphthol is more improved.

(D) A polyethylene glycol more improves the viscosity stability of the oxidative hair dye composition containing (A) α-naphthol. Accordingly, the oxidative hair dye composition preferably includes (D) a polyethylene glycol. The upper limit of the number average molecular weight of (D) the polyethylene glycol is not particularly limited, but is preferably 2,000 or less, more preferably 1,600 or less, and furthermore preferably 1,000 or less. When the number average molecular weight is set to be 2,000 or less, the viscosity stability is more improved. The lower limit of the number average molecular weight of (D) the polyethylene glycol is not particularly limited, but is preferably 100 or more from the viewpoint of the easy availability of the raw materials.

The lower limit of the content of the (D) component in the mixture of the first agent and the second agent is appropriately set, and is preferably 0.1% by mass or more, more preferably 0.5% by mass or more, and furthermore preferably 1% by mass or more. When the content of the (D) component is 0.1% by mass or more, the viscosity stability is more improved. The upper limit of the content of the (D) component in the mixture of the first agent and the second agent is appropriately set, and is preferably 20% by mass or less, more preferably 10% by mass or less, and furthermore preferably 5% by mass or less. When the content of the (D) component is 20% by mass or less, the dyeing property is improved.

(E) A hydroxyalkyl cellulose or a derivative thereof improves the miscibility between the first agent and the second agent at the time of use. For example, even when the oxidative hair dye composition includes the first agent that is a cream formulation and the second agent that is a liquid formulation, the miscibility between the first agent and the second agent is improved. Accordingly, the first agent preferably contains (E) a hydroxyalkyl cellulose or a derivative thereof. Specific examples of the (E) component include hydroxyethyl cellulose, hydroxypropyl cellulose, and hydroxypropyl methyl cellulose. Among these, hydroxy ethyl cellulose is preferable from the viewpoint of being excellent in miscibility.

The lower limit of the content of the (E) component in the first agent is appropriately set, and is preferably 0.01% by mass or more, more preferably 0.05% by mass or more, and furthermore preferably 0.1% by mass or more. When the content of the (E) component is 0.01% by mass or more, the miscibility between the first agent and the second agent at the time of use is more improved.

The upper limit of the content of the (E) component in the first agent is appropriately set, and is preferably 10% by mass or less, more preferably 5% by mass or less, and furthermore preferably 2% by mass or less. When the content of the (E) component is 10% by mass or less, the solubility in the composition is improved.

The alkaline agent contained in the first agent acts to improve the hair dyeing effect by promoting the action of the oxidant contained in the second agent. Examples of the alkaline agent include ammonia, an alkanolamine, a silicate, a carbonate, a hydrogencarbonate, a metasilicate, a sulfate, a chloride, a phosphate, an organic amine, a basic amino acid, and a hydroxide of an alkali metal or an alkaline earth metal. Specific examples of the alkanolamine include monoethanolamine and triethanolamine. Specific examples of the silicate include sodium silicate and potassium silicate. Specific examples of the carbonate include sodium carbonate and ammonium carbonate. Specific examples of the hydrogencarbonate include sodium hydrogencarbonate and ammonium hydrogencarbonate. Specific examples of the metasilicate include sodium metasilicate and potassium metasilicate. Specific examples of the sulfate include ammonium sulfate. Specific examples of the chloride include ammonium chloride. Specific examples of the phosphate include ammonium dihydrogenphosphate and diammonium hydrogenphosphate. Specific examples of the organic amine include 2-amino-2-methyl-1-propanol (AMP), 2-amino-2-methyl-1,3-propanediol, and guanidine. Specific examples of the basic amino acid include arginine and lysine. Specific examples of the hydroxide of an alkali metal or an alkaline earth metal include sodium hydroxide and potassium hydroxide. Only one of these alkaline agents may be contained alone, or two or more of these alkaline agents may be contained in combination. Among these, from the viewpoint of improving the hair dyeing effect, ammonia, an ammonium salt, and an alkanolamine are preferably applied.

The content of the alkaline agent in the mixture of the first agent and the second agent is preferably such that the alkaline agent is mixed in such a way that the pH of the mixture falls within a range between 7 and 12. By regulating the pH of the mixture of the first agent and the second agent so as to be 7 or more, the action of the oxidant contained in the second agent is more promoted. By regulating the pH of the mixture of the first agent and the second agent so as to be 12 or less, the damage of hair due to the application of the oxidative hair dye composition is more suppressed.

The oxidative hair dye composition may further contain, if necessary, the components other than the foregoing components such as a solubilizer, a water-soluble polymer other than the foregoing water soluble polymers, an oily component other than the foregoing oily components, a polyhydric alcohol other than the foregoing polyhydric alcohols, a surfactant other than the foregoing surfactants, a pH adjuster, a sugar, a preservative, a stabilizer, a plant extract, a crude drug extract, a vitamin, a perfume, an antioxidant, a chelating agent, and an ultraviolet absorber.

A solubilizer is mixed, for example, in the case where the first agent is made in a liquid form. Examples of the solubilizer used include water and an organic solvent. Specific examples of the organic solvent include ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anise alcohol, p-methylbenzyl alcohol, α-dimethyl phenethyl alcohol, α-phenylethanol, ethylene glycol phenyl ether (phenoxyethanol), phenoxyisopropanol, 2-benzyloxyethanol, an N-alkylpyrrolidone, an alkylene carbonate, and an alkyl ether. Only one of these solubilizers may be contained alone, or two or more of these solubilizers may be contained in combination. Among these, water is preferably applied because water is excellent in the capability of dissolving the other components in the first agent. When water is used as the solvent, the content of water in the mixture of the first agent and the second agent (the content at the time of use) is preferably 40% by mass or more and more preferably 50% by mass or more.

A water-soluble polymer imparts an appropriate viscosity to the oxidative hair dye composition. Accordingly, the oxidative hair dye composition may contain a water-soluble polymer within a range not impairing the advantageous effects of the present invention. Examples of the water-soluble polymer include a natural polymer, a semisynthetic polymer, a synthetic polymer, and an inorganic polymer. Specific examples of the natural polymer include guar gum, locust bean gum, quince seed, carrageenan, galactan, gum arabic, tragacanth gum, pectin, mannan, xanthan gum, dextran, succinoglucan, curdlan, hyaluronic acid, gelatin, casein, albumin, collagen, dextrin, and triglucopolysaccharide (pullulan).

Specific examples of the semisynthetic polymer include methyl cellulose, ethyl cellulose, carboxy methyl cellulose, sodium carboxy methyl cellulose, cationized cellulose, cationized guar gum, starch phosphate, propylene glycol alginate, and an alginic acid salt. Specific examples of the cationized cellulose include hydroxy ethyl cellulose dimethyl diallyl ammonium chloride.

Specific examples of the synthetic polymer include polyvinyl caprolactam, polyvinyl alcohol (PVA), polyvinylpyrrolidone (PVP), vinylpyrrolidone-vinyl acetate (VP/VA) copolymer, polyvinyl butylal, polyvinyl methyl ether, carboxyvinyl polymer, sodium polyacrylate, polyacrylamide, polyethylene oxide, ethylene oxide-propylene oxide block copolymer, acrylic acid/alkyl acrylate copolymer, polydimethylmethylene piperidinium chloride, and a copolymer composed of a semi-ester of itaconic acid and POE alkyl ether, or an ester of methacrylic acid and a POE alkyl ether, and at least one monomer selected from acrylic acid, methacrylic acid and alkyl esters of these acid. Only one of these water-soluble polymers may be contained alone, or two or more of these water-soluble polymers may be contained in combination.

The oily component imparts a moist feeling to hair. Accordingly, the oxidative hair dye composition may contain an oily component within a range not impairing the advantageous effects of the present invention. Examples of the oily component include an oil/fat, a wax that is in a solid state at 25° C., a higher alcohol that is in a solid state at 25° C., a hydrocarbon, a higher fatty acid, an alkyl glyceryl ether, an ester that is in a solid state at 25° C., and silicone.

Specific examples of the oil/fat include Argania spinosa kernel oil, lanolin, olive oil (purified olive oil), camellia oil, shea fat, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of the wax that is in a solid state at 25° C. include beeswax, candelilla wax, carnauba wax, lanolin wax, rice bran wax, sugarcane wax, insect white wax, palm wax, and montan wax. Specific examples of the higher alcohol that is in a solid state at 25° C. include cetyl alcohol (cetanol), stearyl alcohol, cetostearyl alcohol, arachidyl alcohol, behenyl alcohol, myristyl alcohol, and lanolin alcohol.

Specific examples of the hydrocarbon include paraffin, olefin oligomer, polyisobutene, hydrogenated polyisobutene, a mineral oil, squalane, polybutene, polyethylene, microcrystalline wax, and vaseline. Specific examples of the higher fatty acid include lauric acid, myristic acid, palmitic acid, stearic acid, behenic acid, isostearic acid, 12-hydroxy stearic acid, oleic acid, and lanolin fatty acid. Specific examples of the alkyl glyceryl ether include batyl alcohol, chimyl alcohol, selachyl alcohol, and isostearyl glyceryl ether.

Specific examples of the ester that is in a solid state at 25° C. include butyl stearate, stearyl stearate, cetyl myristate, myristyl myristate, cetyl palmitate, cetyl lactate, myristyl lactate, lanolin acetate, choresteryl stearate, cholesteryl oleate, oleyl oleate, dioctyl succinate, and diethoxyethyl succinate.

Specific examples of the silicone include dimethylpolysiloxane (dimethicone), methylphenylpolysiloxane, decamethylcyclopentasiloxane, dodecamethylcyclohexasiloxane, a terminal hydroxyl group-modified dimethylpolysiloxane, a high polymerization silicone, a polyether-modified silicone (for example, (PEG/PPG/butylene/dimethicone) copolymer), an amino-modified silicone, a betaine-modified silicone, an alkyl-modified silicone, an alkoxy-modified silicone, a mercapto-modified silicone, a carboxy-modified silicone, and a fluorine-modified silicone. Only one of these oily components may be contained alone, or two or more of these oily components may be contained in combination.

Examples of the polyhydric alcohol include a glycol and glycerin. Examples of the glycol include ethylene glycol, propylene glycol, dipropylene glycol, polypropylene glycol, isoprene glycol, and 1,3-butylene glycol. Examples of the glycerin include glycerin, diglycerin, and polyglycerin. Only one of these polyhydric alcohols may be contained alone, or two or more of these polyhydric alcohols may be contained in combination.

The surfactant, as an emulsifying agent or a component for solubilizing the respective components, emulsifies or solubilizes the oxidative hair dye composition, and regulates the viscosity of the oxidative hair dye composition and improves the viscosity stability of the oxidative hair dye composition when the oxidative hair dye composition is used. Accordingly, the oxidative hair dye composition may contain a surfactant within a range not impairing the advantageous effects of the present invention. Examples of the surfactant include an anionic surfactant, a cationic surfactant, an amphoteric surfactant, and a nonionic surfactant other than those described above.

Specific examples of the anionic surfactant include an alkyl ether sulfate, an alkyl sulfate, an alkyl ether sulfate ester salt, an alkenyl ether sulfate, an alkenyl sulfate, an olefin sulfonate, an alkane sulfonate, a saturated or unsaturated fatty acid salt, an alkyl or alkenyl ether carboxylate, an α-sulfofatty acid salt, an N-acylamino acid-type surfactant, a phosphate mono- or di-ester-type surfactant, a sulfosuccinic acid ester, an N-alkyloylmethyl taurine salt, and a drivative thereof. Specific examples of the counterion of the anionic group of these surfactants include sodium ion, potassium ion, and triethanolamine. More specifically, examples of the alkyl ether sulfate ester salt include sodium POE lauryl ether sulfate. Specific examples of the alkyl sulfate include sodium lauryl sulfate and sodium cetyl sulfate. Specific examples of the derivative of the alkyl sulfate include sodium POE lauryl sulfate. Specific examples of the sulfosuccinic acid ester include disodium lauryl sulfosuccinate. Specific examples of the N-alkyloylmethyl taurine salt include sodium N-stearoyl-N-methyltaurate.

Specific examples of the cationic surfactant include lauryl trimethyl ammonium chloride, cetyl trimethyl ammonium chloride, stearyl trimethyl ammonium chloride, alkyl trimethyl ammonium chloride, distearyl dimethyl ammonium chloride, cetyl trimethyl ammonium bromide, stearyl trimethyl ammonium bromide, lanolin fatty acid aminopropyl ethyl dimethyl ammonium ethyl sulfate, stearyl trimethyl ammonium saccharin, cetyl trimethyl ammonium saccharin, methacryloyloxy ethyl trimethylammonium chloride, behenyl trimethyl ammonium methyl sulfate, behenyl dimethyl amine, behenic acid diethyl aminoethyl amide, behenic acid dimethyl aminopropyl amide, behenic acid dimethyl aminoethyl amide, stearyl dimethyl amine, palmitoxypropyl dimethylamine, stearoxypropyl dimethylamine, and stearic acid dimethyl aminopropyl amide. Specific examples of the alkyl trimethyl ammonium chloride include behenyl trimethyl ammonium chloride and arachidyl trimethyl ammonium chloride.

Specific examples of the amphoteric surfactant include coco-betaine, lauramidopropyl betaine, cocamidopropyl betaine, sodium lauroamphoacetate, sodium cocoamphoacetate, coconut oil fatty acid amidopropyl betaine, lauryl betaine (betaine lauryldimethylamino acetate), and sodium laurylaminopropionate.

Specific examples of the nonionic surfactant include an ether-type nonionic surfactant, an ester-type nonionic surfactant, and an alkyl glucoside. Specific examples of the ether-type nonionic surfactant include the following each having a POE chain having a number of moles of added EO of 19 or less: POE cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, POE polyoxypropylene cetyl ether, POE polyoxypropylene decyl tetradecyl ether.

Specific examples of the ester-type nonionic surfactant include the following each having a POE chain having a number of moles of added EO of 19 or less: POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbit tetraoleate, POE sorbit hexastearate, POE sorbit monolaurate, POE sorbit beeswax, polyethylene glycol monooleate, polyethylene glycol monostearate, and polyethylene glycol monolaurate; and lipophilic glycerin monooleate, lipophilic glycerin monostearate, self-emulsifying glycerin monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Specific examples of the alkyl glucoside include an alkyl (having 8 to 16 carbon atoms) glucoside and alkyl glucosides each having a POE chain having a number of moles of added EO of 19 or less such as POE methyl glucoside and POE methyl glucoside dioleate. Only one of these specific examples of the surfactant may be contained alone, or two or more of these specific examples of the surfactant may be contained in combination.

The pH adjuster may be mixed in order to adjust the pH of the oxidative hair dye composition. The pH adjuster may be selected from the known pH adjusters. Examples of the pH adjuster include an inorganic acid, an organic acid, and a salt thereof. Specific examples of the organic acid include citric acid, glycolic acid, succinic acid, tartaric acid, lactic acid, malic acid, levulinic acid, acetic acid, butyric acid, valeric acid, oxalic acid, maleic acid, fumaric acid, and mandelic acid. Specific examples of the organic acid salt include a sodium salt, a potassium salt, and an ammonium salt. Specific examples of the inorganic acid include phosphoric acids such as phosphoric acid and pyrophosphoric acid, hydrochloric acid, sulfuric acid, and nitric acid. These may be used each alone, or in combinations of two or more thereof.

Specific example of the sugar include: monosaccharides such as glucose and galactose; disaccharides such as maltose, sucrose, fructose, and trehalose; and a sugar alcohol. Specific examples of the preservative include paraben, methylparaben, and sodium benzoate. Specific examples of the stabilizer include phenacetin, 8-hydroxyquinoline, acetanilide, sodium pyrophosphate, barbituric acid, uric acid, and tannic acid. Specific examples of the antioxidant include ascorbic acids and sulfites. Specific examples of the chelating agent include edetic acid (ethylenediaminetetraacetic acid (EDTA)), disodium edetate, tetrasodium edetate, diethylenetriaminepentaacetic acid and salts thereof, ethylenediaminehydroxyethyl triacetic acid and salts thereof, and hydroxyethane diphosphonic acid (HEDP) and salts thereof.

The formulation of the first agent is not particularly limited; specific examples of the formulation include the formulations that are in a liquid state such as an aqueous solution or an emulsion, a gel state, a foam state, a cream state, and a solid state at 25° C. Among these, the cream formulation is preferable from the viewpoint of exhibiting the application property to hair and the miscibility of different types of agents at the same time.

(Second Agent of Two-Part Type Oxidative Hair Dye Composition)

The second agent may contain the foregoing solubilizer and the like in addition to the oxidant. The oxidant more improves the decolorization property for melanin contained in hair. Specific examples of the oxidant include hydrogen peroxide, urea peroxide, melamine peroxide, sodium percarbonate, potassium percarbonate, sodium perborate, potassium perborate, ammonium persulfate, potassium persulfate, sodium persulfate, sodium peroxide, potassium peroxide, magnesium peroxide, barium peroxide, calcium peroxide, strontium peroxide, hydrogen peroxide adducts of sulfates, hydrogen peroxide adducts of phosphates, and hydrogen peroxide adducts of pyrophosphates. Only one of these specific examples of the oxidant may be contained alone, or two or more of these specific examples may be contained in combination. The content of the oxidant in the second agent is appropriately set, and is preferably 0.1% by mass or more, more preferably 2% by mass or more, and furthermore preferably 3% by mass or more. When the content of the oxidant is 0.1% by mass or more, the decolorization property for melanin is more improved. The content of the oxidant in the second agent is preferably 15% by mass or less, more preferably 9% by mass or less, and furthermore preferably 6% by mass or less. When the content of the oxidant is 15% by mass or less, the damage of hair and the like can be more suppressed.

When hydrogen peroxide is mixed in the second agent as an oxidant, for the purpose of improving the stability of hydrogen peroxide, the second agent preferably contains a stabilizer such as sodium stannate, ethylene glycol phenyl ether (phenoxyethanol), hydroxyethane diphosphonic acid and a salt thereof. Examples of the hydroxyethane diphosphonic acid salt include tetrasodium hydroxyethane diphosphonate and disodium hydroxyethane diphosphonate. The second agent may contain the components that are generally contained in an oxidative hair dye composition and that do not disturbing the actions of the foregoing respective components. For example, the second agent may optionally contain the foregoing components contained in the first agent within the ranges not impairing the advantageous effects of the present invention.

The formulation of the second agent is not particularly limited; specific examples of the formulation include the formulations that are in a liquid state such as an aqueous solution or an emulsion, a gel state, a foam state, a cream state and a solid state at 25° C. When for the first agent a cream-state formulation is adopted, the formulation of the second agent is preferably a formulation in a liquid state such as an emulsion from the viewpoint of improving the miscibility with the first agent.

<Three-or-More-Part Type Oxidative Hair Dye Composition>

For example, the first agent of a two-part type oxidative hair dye composition may be divided into an agent containing the alkaline agent and an agent containing the components other than the alkaline agent, to thereby constitute a three-part type oxidative hair dye composition. In this case, the three-part type oxidative hair dye composition has satisfactory formulation stability. In this way, from the viewpoint of the formulation stability and the like, the respective components contained in the first agent or the second agent may be stored as divided into a plurality of agents. Even when the oxidative hair dye composition is constituted as a three or more part type, such an oxidative hair dye composition is still included in the present invention as long as the advantageous effects of the present invention are achieved.

<Preparation of Oxidative Hair Dye Composition Mixture>

In the oxidative hair dye composition, the foregoing respective agents are mixed with each other at the time of use, and thus a mixture is prepared when the oxidative hair dye composition is used. In the preparation of the mixture, the mixture may be prepared by placing predetermined amounts of the respective agents in an airtight container having a predetermined volume and by shaking and mixing the respective agents together. Alternatively, the mixture may also be prepared by placing the respective agents in a vessel such as a tray and by stirring and mixing the respective agents together with a brush, a stirring rod, or the like. For example, in the case where the first agent is a cream formulation and the second agent is liquid, mixing by shaking by using a tubular airtight container having a volume of 100 to 300 mL is preferable from the viewpoint of easy mixing operation. The total volume of the mixture in the container is preferably 20 to 80% by volume relative to the internal volume of the airtight container from the viewpoint of improving the miscibility. The shaking-mixing with an airtight container containing the respective agents placed therein may be performed by manual up-and-down/right-and-left reciprocating motion, or may be performed mechanically by using a vibration exciter or the like. The obtained mixture of the oxidative hair dye composition is applied to hair in a just necessary amount by using, for example, hands with thin gloves, a comb, or a brush, or a container with a lid having a discharge opening or with a comb.

When the mixture is applied to hair by using a container with a lid having a discharge opening or with a comb, the viscosity of the mixture at 25° C. is preferably 3,000 to 10,000 millipascal second (mPa·s) and more preferably 4,000 to 9,000 mPa·s. When the viscosity of the mixture falls within such a range, it is possible to improve the discharging property and the application property from a container with a lid having a discharge opening or with a comb. The viscosity of the mixture can be determined by using, for example, a B-type viscometer under the measurement conditions of 25° C. and 1 minute. Specific examples of the B-type viscometer include a BL-type viscometer (manufactured by Toki Sangyo Co., Ltd.). The rotor used and the rotation speed are appropriately selected according to the measurable viscosity range of the measurement apparatus. For example, a viscosity can be determined by using a size 3 rotor under the condition of 120 rpm. The viscosity of the mixture can be appropriately regulated by varying the mixing proportions of, for example, the foregoing solubilizer, water-soluble polymer, oily component and surfactant.

The oxidative hair dye composition according to the present embodiment has the following advantages.

(1) In addition to a predetermined amount of (A) α-naphthol, the oxidative hair dye composition according to the present embodiment contains (B) an oily component that is in a liquid state at 25° C. such as a higher alcohol and (C) a nonionic surfactant having a POE chain having a number of moles of added EO of 20 or more. Accordingly, in the oxidative hair dye composition using α-naphthol, the viscosity stability is improved. In particular, even when the viscosity of the mixture of the oxidative hair dye composition at 25° C. is as low as 3,000 to 10,000 mPa·s, the decrease of the viscosity is suppressed, and the degradation of the application property such as dripping is suppressed.

(2) In addition to (A) α-naphthol in the first agent, the oxidative hair dye composition according to the present embodiment contains a predetermined proportion of (B) an oily component that is in a liquid state at 25° C. such as a higher alcohol and (C) a nonionic surfactant having a POE chain having a number of moles of added EO of 20 or more. Accordingly, the viscosity stability of the first agent containing α-naphthol is improved. The formulation stability of the first agent is also improved.

(3) In a constitution where the oxidative hair dye composition includes the first agent that is a cream formulation and the second agent that is a liquid formulation and the first agent and the second agent are mixed with each other at the time of use by shaking in an airtight container, when the first agent further contains (E) a hydroxyalkyl cellulose or a derivative thereof, the miscibility between the first agent and the second agent is improved.

The above-described embodiment may be modified as follows.

The oxidative hair dye composition of the above-described embodiment achieves advantageous effects of the present invention when the (A) to (D) components are contained in the mixture at the time of use. Accordingly, when the oxidative hair dye composition is constituted as a two or more part type formulation, the (A) to (D) components may be contained in any of the agents during storage.

In the above-described embodiment, some of the components contained in the first agent, the second agent, or the third agent of the oxidative hair dye composition may constitute an additional agent to increase the number of the agents constituting the oxidative hair dye composition.

The viscosity range of the first agent or the second agent is not particularly limited. However, in the case of an emulsion formulation, the viscosity at 25° C. is preferably 3,000 to 10,000 mPa·s, and in the case of a cream or gel formulation, the viscosity at 25° C. is preferably 10,000 to 50,000 mPa·s. The viscosity can be measured by using, for example, a B-type viscometer, on the basis of the same method as described above.

In the embodiment, a direct dye listed in, for example, "The Japanese Standards of Quasi-Drug Ingredients" (published by Yakuji Nippo Ltd., June 2006) may be optionally contained as a dye other than the foregoing oxidative dye, within a range not impairing the advantageous effects of the present invention.

EXAMPLES

Next, the foregoing embodiments will be described more specifically with reference to Examples and Comparative Examples. The present invention is not limited to the constitutions described in the Examples section.

As the oxidative hair dye compositions, first agents that were cream formulations and contained the components shown in Table 1 or 2, and second agents that were emulsion formulations and contained the components shown in Table 3 were prepared. It is to be noted that the numerical values in the rows of the respective components in the respective tables show the contents of the components concerned and the units thereof are percent by mass. The symbols (A) to (E) in the "Components" columns in the tables represent the compounds corresponding to the respective components described in the claims of the present application. The symbol "c" in the "Components" column in the table represents a compound for comparison with the component described in the claim of the present application. The formulation stability of the first agent was evaluated by the following method.

Next, the first agent and the second agent were mixed with each other in a ratio of 2:3 to prepare a mixture of the oxidative hair dye composition. The mixing operation of the first agent and the second agent was performed by using a cylindrical airtight lidded container (internal volume: 200 mL) of 12 cm in height and 4.5 cm in diameter. The container was charged with a total volume of 120 mL of the first agent and the second agent, and then the container was shaken in an up-and-down direction 30 times as reciprocating motion, and thus, the first agent and the second agents were mixed with each other. The viscosity of the obtained mixture was measured under the following conditions. The miscibility in the mixing of the first agent and the second agent was evaluated by the following method. The viscosity can be determined by using, as a B-type viscometer, a BL-type viscometer (manufactured by Toki Sangyo Co., Ltd.) and a size 3 rotor, under the conditions of 120 rpm and 25° C.

(Formulation Stability of First Agent)

The first agent of each of Reference Example, Examples and Comparative Examples was placed in a glass bottle, and stored in a thermostatic chamber at 60° C. for 24 hours; then the separation state of the first agent was visually evaluated, and thus it was determined whether or not the retention effect of the first agent, which was in a cream state, was satisfactory. The case where no separation was observed was evaluated as 5, the case where a slight separation was observed was evaluated as 3, the case where a considerable separation was observed was evaluated as 1; the cases corresponding to the intermediates of these three cases were evaluated as 4 and 2, respectively. The results thus obtained are shown in the tables presented below.

(Viscosity Stability of Mixture)

In comparison to Example 1, an oxidative hair dye composition of Reference Example 1 was prepared by using a first agent of the oxidative hair dye composition not containing α-naphthol. Immediately after the preparation of the mixture of each of Reference Example, Examples and Comparative Examples, within 1 minute, the viscosity of the mixture was measured under the same conditions as described above. From the viscosity of the mixture of each of Examples and Comparative Examples and the viscosity of the mixture of Reference Example 1, the viscosity difference (the viscosity of the mixture of Reference Example 1 minus the viscosity of the mixture of each of Examples and Comparative Examples) was calculated.

A smaller viscosity difference indicates a better viscosity stability of the mixture. The cases where the absolute value of the viscosity difference was less than 500 mPa·s, 500 mPa·s or more and less than 1,500 mPa·s, 1,500 mPa·s or more and less than 2,000 mPa·s, 2,000 mPa·s or more and less than 2,500 mPa·s, and 2,500 mPa·s or more were evaluated as 5, 4, 3, 2, and 1, respectively. The results thus obtained are shown in the tables presented below.

(Miscibility)

Five panelists charged airtight lidded containers with the first agent and the second agent, shook the containers gently 10 times in the up-down direction, then visually evaluated the state of the mixture, namely, the mixing degree after the shaking on the basis of the following standards, and thus determined the miscibility. The miscibility of the mixture was scored on the basis of the following 5-point scale: the case where any nonuniform portion was absolutely absent was evaluated as 5, the case where nonuniform portions were nearly absent was evaluated as 4, the case where nonuniform portions slightly remained was evaluated as 3, the case where nonuniform portions were easily found to remain was evaluated as 2, and the case where nonuniform portions remained to a large extent was evaluated as 1. The scoring results of the panelists were averaged. The mixture was rated as "excellent: 5", "good: 4", "fair: 3", "slightly poor: 2", or "poor: 1" when the average score was 4.6 points or more, 3.6 points or more and less than 4.6 points, 2.6 points or more and less than 3.6 points, 1.6 points or more and less than 2.6 points, or less than 1.6 points, respectively. The results thus obtained are shown in the tables presented below.

TABLE 1

| Components of first agent | Reference Example 1 | Example 1 | Example 2 | Example 3 | Example 4 | Example 5 | Example 6 | Example 7 |
|---|---|---|---|---|---|---|---|---|
| p-Toluylenediamine sulfate | 3.5 | 3.5 | 3.5 | 3.5 | 3.5 | 3.5 | 3.5 | 3.5 |
| Resorcin | 0.5 | 0.5 | 0.5 | 0.5 | 0.5 | 0.5 | 0.5 | 0.5 |
| m-Aminophenol | 0.2 | 0.2 | 0.2 | 0.2 | 0.2 | 0.2 | 0.2 | 0.2 |
| (A) α-Naphthol | — | 0.2 | 0.6 | 0.2 | 0.2 | 0.2 | 0.2 | 0.2 |
| (B) 2-Octyldodecanol | 1 | 1 | 1 | 0.1 | 2 | — | 3 | 1 |
| (B) Cetyl octanoate | — | — | — | — | — | 1 | — | — |
| (C) POE(50) oleyl ether | 1 | 1 | 1 | 1 | 1 | 1 | 1 | — |
| POE(20) cetyl ether | 2 | 2 | 2 | 2 | 2 | 2 | 2 | 3 |
| POE(2) stearyl ether | 2.5 | 2.5 | 2.5 | 2.5 | 2.5 | 2.5 | 2.5 | 2.5 |
| Behenyl trimethyl ammonium chloride (number of carbon atoms: 22) | 1 | 1 | 1 | 1 | 1 | 1 | 1 | 1 |
| Behenyl alcohol | 0.5 | 0.5 | 0.5 | 0.5 | 0.5 | 0.5 | 0.5 | 0.5 |
| Stearyl alcohol | 7 | 7 | 7 | 7 | 7 | 7 | 7 | 7 |
| (E) Hydroxyethyl cellulose | 0.5 | 0.5 | 0.5 | 0.5 | 0.5 | 0.5 | 0.5 | 0.5 |
| (D) Polyethylene glycol (number average molecular weight: 400) | 7 | 7 | 7 | 7 | 7 | 7 | 7 | 7 |
| Vaseline | 1 | 1 | 1 | 1 | 1 | 1 | 1 | 1 |
| Polydimethylmethylene piperidinium chloride solution (40% by mass) | 1 | 1 | 1 | 1 | 1 | 1 | 1 | 1 |
| L-Ascorbic acid | 0.3 | 0.3 | 0.3 | 0.3 | 0.3 | 0.3 | 0.3 | 0.3 |
| Trisodium hydroxyethyl ethylenediamine triacetate solution (40% by mass) | 0.5 | 0.5 | 0.5 | 0.5 | 0.5 | 0.5 | 0.5 | 0.5 |
| Anhydrous sodium sulfite | 0.2 | 0.2 | 0.2 | 0.2 | 0.2 | 0.2 | 0.2 | 0.2 |
| 28% by mass Ammonia water | 1 | 1 | 1 | 1 | 1 | 1 | 1 | 1 |
| 70% by mass Monoethanolamine | 6 | 6 | 6 | 6 | 6 | 6 | 6 | 6 |
| Purified water | Balance | Balance | Balance | Balance | Balance | Balance | Balance | Balance |
| Total | 100 | 100 | 100 | 100 | 100 | 100 | 100 | 100 |
| Content of A component in mixture | 0 | 0.08 | 0.24 | 0.08 | 0.08 | 0.08 | 0.08 | 0.08 |
| Content of B component in mixture | 0.4 | 0.4 | 0.4 | 0.04 | 0.8 | 0.4 | 1.2 | 0.4 |
| Content of C component in mixture | 1.2 | 1.2 | 1.2 | 1.2 | 1.2 | 1.2 | 1.2 | 1.2 |
| Content of B component/content of C component | 0.33 | 0.33 | 0.33 | 0.03 | 0.67 | 0.33 | 1 | 0.33 |
| Viscosity value (mPa·s) of first agent | 22,280 | 23,990 | 17,740 | 19,630 | 24,680 | 23,810 | 23,180 | 23,550 |
| Viscosity value (mPa·s) of mixture | 5,090 | 4,590 | 3,220 | 3,790 | 4,890 | 5,290 | 5,760 | 3,550 |
| Viscosity difference from Reference Example 1 | — | −500 | −1,870 | −1,300 | −200 | 200 | 670 | −1,540 |
| Viscosity stability of mixture | — | 5 | 3 | 4 | 5 | 5 | 4 | 3 |
| Formulation stability of first agent | 5 | 5 | 4 | 5 | 5 | 5 | 3 | 4 |
| Miscibility | 5 | 5 | 5 | 5 | 5 | 5 | 5 | 5 |

TABLE 2

| Components of first agent | Example 8 | Example 9 | Example 10 | Comp. Example 1 | Comp. Example 2 | Comp. Example 3 | Comp. Example 4 |
|---|---|---|---|---|---|---|---|
| p-Toluylenediamine sulfate | 3.5 | 3.5 | 3.5 | 3.5 | 3.5 | 3.5 | 3.5 |
| Resorcin | 0.5 | 0.5 | 0.5 | 0.5 | 0.5 | 0.5 | 0.5 |
| m-Aminophenol | 0.2 | 0.2 | 0.2 | 0.2 | 0.2 | 0.2 | 0.2 |
| (A) α-Naphthol | 0.2 | 0.2 | 0.2 | 0.2 | 0.2 | 1.2 | 1.2 |
| (B) 2-Octyldodecanol | 1 | 1 | 1 | — | 1 | 1 | 1 |
| (C) POE(50) oleyl ether | 1 | 1 | 1 | 1 | — | 1 | 3 |
| POE(20) cetyl ether | 2 | 2 | 2 | 2 | — | 2 | 6 |
| c POE(10) cetyl ether | — | — | — | — | 3 | — | — |
| POE(2) stearyl ether | 2.5 | 2.5 | 2.5 | 2.5 | 2.5 | 2.5 | 2.5 |

TABLE 2-continued

| Components of first agent | Example 8 | Example 9 | Example 10 | Comp. Example 1 | Comp. Example 2 | Comp. Example 3 | Comp. Example 4 |
|---|---|---|---|---|---|---|---|
| Behenyl trimethyl ammonium chloride (number of carbon atoms: 22) | 1 | 1 | 1 | 1 | 1 | 1 | 1 |
| Behenyl alcohol | 0.5 | 0.5 | 0.5 | 1.5 | 0.5 | 0.5 | 0.5 |
| Stearyl alcohol | 7 | 7 | 7 | 7 | 7 | 7 | 7 |
| (E) Hydroxyethyl cellulose | 0.5 | 0.5 | — | 0.5 | 0.5 | 0.5 | 0.5 |
| (D) Polyethylene glycol (number average molecular weight: 400) | 3 | — | 7 | 7 | 7 | 7 | 7 |
| Vaseline | 1 | 1 | 1 | 1 | 1 | 1 | 1 |
| Polydimethylmethylene piperidinium chloride solution (40% by mass) | 1 | 1 | 1.7 | 1 | 1 | 1 | 1 |
| L-Ascorbic acid | 0.3 | 0.3 | 0.3 | 0.3 | 0.3 | 0.3 | 0.3 |
| Trisodium hydroxyethyl ethylenediamine triacetate solution (40% by mass) | 0.5 | 0.5 | 0.5 | 0.5 | 0.5 | 0.5 | 0.5 |
| Anhydrous sodium sulfite | 0.2 | 0.2 | 0.2 | 0.2 | 0.2 | 0.2 | 0.2 |
| 28% by mass Ammonia water | 1 | 1 | 1 | 1 | 1 | 1 | 1 |
| 70% by mass Monoethanolamine | 6 | 6 | 6 | 6 | 6 | 6 | 6 |
| Purified water | Balance | Balance | Balance | Balance | Balance | Balance | Balance |
| Total | 100 | 100 | 100 | 100 | 100 | 100 | 100 |
| Content of A component in mixture | 0.08 | 0.08 | 0.08 | 0.08 | 0.08 | 0.48 | 0.48 |
| Content of B component in mixture | 0.4 | 0.4 | 0.4 | 0 | 0.4 | 0.4 | 0.4 |
| Content of C component in mixture | 1.2 | 1.2 | 1.2 | 1.2 | 0 | 1.2 | 3.6 |
| Content of B component/content of C component | 0.33 | 0.33 | 0.33 | — | — | 0.33 | 0.11 |
| Viscosity value (mPa · s) of first agent | 21,360 | 18,360 | 14,580 | 22,060 | 17,060 | 25,440 | 7,950 |
| Viscosity value (mPa · s) of mixture | 4,430 | 3,440 | 5,590 | 3,030 | 1,600 | — | — |
| Viscosity difference from Reference Example 1 | −660 | −1,650 | 500 | −2,060 | −3,490 | — | — |
| Viscosity stability of mixture | 4 | 3 | 5 | 2 | 1 | — | — |
| Formulation stability of first agent | 5 | 5 | 5 | 5 | 5 | 1 | 1 |
| Miscibility | 5 | 5 | 3 | 5 | 5 | — | — |

TABLE 3

| Components of second agent (emulsion formulation) | |
|---|---|
| 35% by mass Hydrogen peroxide | 15 |
| Cetanol | 1 |
| POE(10) cetyl ether (HLB: 13.5) | 0.2 |
| Stearyl trimethyl ammonium chloride | 0.2 |
| Hydroxyethane diphosphinic acid | 0.05 |
| Tetrasodium hydroxyethane diphosphonate | 0.05 |
| Purified water | Balance |
| Total | 100 |

As shown in Tables 1 and 2, each of Examples was determined to have the results that each of the evaluation items was rated as 3 or higher. Comparative Example 1 not containing the (B) component was determined to be poor in the evaluation of the viscosity stability as compared with each of Examples. Comparative Example 2 not containing the (C) component was determined to be poor in the evaluation of the viscosity stability as compared with each of Examples. Comparative Examples 3 and 4 each having a large content of (A) α-naphthol were determined to be poor in the evaluation of the stability of the first agent. It is to be noted that Comparative Examples 3 and 4 were poor in the stability of the first agent, and accordingly the evaluation of the miscibility was not performed for Comparative Examples 3 and 4.

The foregoing embodiment and Examples are presented as exemplification for describing the present invention, and the present invention is not limited to the foregoing embodiment and Examples. For the embodiment disclosed for exemplification, various alternatives, alterations and modifications can be made without departing from the gist and scope of the present invention. For example, the subject of the present invention may possibly reside in features smaller in number than all the features of the particular disclosed embodiment. Accordingly, the scope of the claims of the invention is incorporated into the detailed description, and each of the claims itself claims a separate embodiment. The scope of the present invention is intended to include, in the scope of the claims, all of such alternative forms, alteration forms and modification forms, together with all the equivalents of these forms.

The invention claimed is:

1. An oxidative hair dye composition comprising an alkaline agent and an oxidant, wherein the oxidative hair dye composition includes:

(A) α-naphthol in a content of 0.005 to 0.45% by mass;
(B) at least one oily component in a content of 0.01 to 5% by mass, the at least one oily component is selected from the group consisting of a higher alcohol, an ester, and a wax that are in a liquid state at 25° C.;
(C) a nonionic surfactant having a polyoxyethylene chain having a number of moles of added ethylene oxide of 20 or more; and
(D) a polyethylene glycol having a number average molecular weight of 400 or more, wherein
the mass ratio of the content of the (B) component to the content of the (C) component is 0.01 to 1.5.

2. The oxidative hair dye composition according to claim 1, wherein the viscosity of the oxidative hair dye composition at the time of use is 3,000 to 10,000 mPa·s at 25° C.

3. The oxidative hair dye composition according to claim 1, comprising:
a first agent containing the alkaline agent and being a cream formulation; and
a second agent containing the oxidant and being a liquid formulation, wherein
the first agent and the second agent are mixed with each other in an airtight container at the time of use; and
the first agent further contains (E) a hydroxyalkyl cellulose or a derivative thereof.

* * * * *